United States Patent
Mörchel et al.

(10) Patent No.: US 11,457,814 B2
(45) Date of Patent: Oct. 4, 2022

(54) APPARATUS FOR DETERMINING A DISEASE PARAMETER

(71) Applicants: Fraunhofer-Gesellschaft, Munich (DE); Julius-Maximilians-Universität Würzburg, Würzburg (DE)

(72) Inventors: Philipp Mörchel, Zell am Main (DE); Johannes Oberberger, Würzburg (DE)

(73) Assignees: FRAUNHOFER-GESELSCHAFT, Zell am Main (DE); JULIUS-MAXIMILIANS-UNIVERSITÄT WÜRZBURG, Würzburg (DE)

(*) Notice: Subject to any disclaimer, the term of this patent is extended or adjusted under 35 U.S.C. 154(b) by 315 days.

(21) Appl. No.: 16/424,895

(22) Filed: May 29, 2019

(65) Prior Publication Data
US 2019/0313911 A1 Oct. 17, 2019

Related U.S. Application Data (63) Continuation of application No. PCT/EP2017/080471, filed on Nov. 27, 2017.

(30) Foreign Application Priority Data

Dec. 1, 2016 (EP) .................................. 16201753

(51) Int. Cl.
*G16H 50/20* (2018.01)
*A61B 5/055* (2006.01)
(Continued)

(52) U.S. Cl.
CPC ............ *A61B 5/0044* (2013.01); *A61B 5/055* (2013.01); *G06V 10/76* (2022.01); *G16H 50/20* (2018.01)

(58) Field of Classification Search
CPC .......... A61B 5/0044; A61B 5/055; A61B 5/24; A61B 2576/023; G16H 50/20; G16H 40/63; G06K 9/6214
See application file for complete search history.

(56) References Cited

U.S. PATENT DOCUMENTS

| 2009/0318803 A1 | 12/2009 | Abe et al. |
| 2013/0197881 A1* | 8/2013 | Mansi .................. A61N 1/3627 703/2 |
| 2014/0071125 A1 | 3/2014 | Burlina et al. |

FOREIGN PATENT DOCUMENTS

| WO | 2015200552 A1 | 12/2015 | |
| WO | WO-2015200552 A1 * | 12/2015 | ........... G06T 11/003 |

OTHER PUBLICATIONS

Peter, K. B. (Dec. 12, 2005). Introduction to Diffusion Tensor Imaging Mathematics: Part I. Tensors, Rotations, and Eigenvectors. http://pfeifer.phas.ubc.ca/refbase/files/Kingsley-ConceptsInMagnetic-2006-28a-101.pdf. (Year: 2005).*

(Continued)

*Primary Examiner* — Catherine B Kuhlman
*Assistant Examiner* — Nicholas A Robinson
(74) *Attorney, Agent, or Firm* — Dorsey & Whitney LLP (57) ABSTRACT

An apparatus for determining a disease parameter describing a type of cardiac disease includes a unit for reading input parameters representing 3D myocardial velocity fields with voxel wise 3D velocity information. The velocity vectors represent velocity of a voxel of a region of the heart at a predefined time point or time interval; a velocity vector depicts a voxel wise 3D velocity of the myocardium with different magnitude. A processor applies an algorithm to obtain a rotation parameter and/or strain-rate-tensor representing local curl of the input parameters and local rate of strain at a certain spatial point, at a certain time point or time interval. A processor calculates the disease parameter on the (Continued)

basis of the rotation parameter and strain-rate-tensor, dividing an absolute value of the rotation parameter by an eigenvalue. The disease parameter reflects a proportion to overall deformation of local layer shearing with regard to local pure deformation.

5 Claims, 6 Drawing Sheets

(51) Int. Cl.
    *A61B 5/00*     (2006.01)
    *G06V 10/75*     (2022.01)

(56)     References Cited

OTHER PUBLICATIONS

Dandel M, Lehmkuhl H, Knosalla C, Suramelashvili N, Hetzer R. Strain and strain rate imaging by echocardiography—basic concepts and clinical applicability. Curr Cardiol Rev. 2009;5(2):133-148. doi:10.2174/157340309788166642 (Year: 2009).*
International Search Report and Written Opinion dated Feb. 20, 2018 in connection with International Patent Application No. PCT/EP2017/080471, 11 pages.

* cited by examiner

APPARATUS FOR DETERMINING A DISEASE PARAMETER

CROSS-REFERENCE TO RELATED APPLICATIONS

This application is a continuation of International Application PCT/EP2017/080471, filed Nov. 27, 2017, which claims priority to European Patent Application EP 16201753.7, filed Dec. 1, 2016, entitled "Method and Apparatus for Determining a Disease Parameter," each of which is incorporated by reference herein, in the entirety and for all purposes.

BACKGROUND

Left ventricular cardiac biomechanics is far beyond being fully understood, but it is of crucial importance for the hemodynamical function of the heart in health and in pathologies. As the heart pumps blood by reduction of intraventricular volume, it is desirable to understand this mechanical action from the microscopic level of fibre shortening over cooperation and arrangement of this contraction towards systolic wall thickening and the complementary diastolic relaxation. Since pathologies might affect different steps within this cascade, their assessment by imaging techniques is of great interest. The biomechanics of the left ventricular myocardium is of crucial importance for the hemodynamic function of the heart. However, how global systolic function emerges from microscopic muscle fiber contraction is not fully understood. Aspects as the arrangement and orientation of muscle fibers, and fiber sliding, which itself depends on the extracellular matrix composition should play an important role in myocardial wall thickening.

A simple example will illustrate this: As myocardial fibers shorten, they broaden by reason of incompressibility. But this pure systolic shortening of about 10-15% of the myofibre length can only account for about 8% increase in myocyte diameter and cannot fully explain the observed wall thickening of more than 40%. Thus there must be a mechanism of amplification of the effect of the myofibre contraction.

DISCLOSURE

One histologically reasonable mechanism would be interlaminar shearing, i.e. shearing motion between histological entities within the myocardium, which can be seen as the main mechanism of left ventricular wall thickening and the complementary diastolic relaxation. Therefore, a hypothesis suggests, that intramyocardial shearing motion is the main mechanism of LV-myocardial wall thickening.

Recently the inventors developed a mathematical method for investigating the local myocardial shear-rate from 3D myocardial velocity fields. This new approach, which was called "keirometry" (Greek: keirein: to shear, to metron: the measure), allows to demonstrate that myocardial wall thickening emerges mainly from shear movement. The hypothesis to tackle is that intramyocardial shearing is the main mechanism of myocardial wall thickening.

The verification of this hypothesis would have paramount implications on our understanding of cardiac contraction and relaxation in health and disease. For example, it might explain the effectiveness of systolic myocardial contraction or it could clarify a crucial mechanism of the transition towards heart failure in the chronically infarcted heart, hypertrophy and in several other cardiac pathologies, which might not only be understood better, but also be more diagnostically distinguishable. As the method is equally applicable to shearing motion in systole and to the re-shearing in diastole, it is very promising to assess not only systolic but also diastolic heart failure, which is mechanically poorly understood and where new parameters for its quantification and stratification are most desirable as there is a certain lack of valid non-invasive parameters for diastolic dysfunction.

SUMMARY

In order to better diagnose cardiac disease of the patient the present invention provides a method for determining a disease parameter describing or indicating a type of cardiac disease or a presumed type of cardiac disease. The method comprises the following steps:

Reading in a set of input parameters, wherein the input parameters represent a field of velocity vectors, each velocity vector representing a velocity of motion of a voxel of a region of the heart at a predefined time point;

Applying a processing algorithm on the set of input parameters in order to obtain at least a rotation parameter and/or at least a strain-rate-tensor for each voxel, the rotation parameter representing the local curl of the set of input parameters and the strain-rate-tensor representing a local rate of strain at a certain special point at a certain time point; and Calculating at least the disease parameter on the basis of the rotation parameter and/or the strain-rate-tensor.

Thus, an input parameter can be considered as a velocity vector. Here, input parameters are velocity vectors, building a velocity field. A voxel is a volume unit at a predefined position within a considered field of view or volume of interest, containing for example the myocardial wall. In particular, for every considered (myocardial) voxel a velocity vector is available, representing the instantaneous velocity. A voxel can be considered as a volume unit in a predefined position of the heart or a region of the heart. The velocity vector of a corresponding voxel represents the velocity of motion of the wall of the heart or a region of the wall of the heart. The velocity vectors are measured for a predefined time point or time interval within the cardiac cycle. Different sets can be measured for different time points within the heart cycle in order to evaluate the complete heart cycle. A processing algorithm is a set of processing rules which have to be applied on the set of input parameters in order to obtain at least the rotation parameter and/or strain-rate-tensor. The rotation parameter can be considered as a parameter representing the local voxel wise curl as well as for each time point respectively each time interval. The strain-rate-tensor can be considered as a parameter representing a local voxel wise rate of strain for the set of input parameters. A disease parameter can be considered as a parameter whose value provides information on a type of cardiac disease. Therefore, this disease parameter can be compared with a reference value in order to provide information about the possible cardiac disease of the patient to a physician.

The present invention is based on the finding that the disease parameter, which provides information about the type of cardiac disease, can be generated by an analysis of the set of input parameters, which themselves represent the field of velocity vectors. Especially the determination of the rotation parameter in the form of the curl of the set of input parameters and/or the strain-rate-tensor provides the basis for calculating a set of disease parameters in order to provide very precise information about the type of cardiac disease to a physician.

EXAMPLES

According to a preferred embodiment of the present invention the step of Applying the processing algorithm comprises a calculation of at least the Jacobian matrix from the set of input parameters, particularly in order to calculate the strain-rate-tensor. Such an embodiment of the present invention provides the advantage that the movement of the voxel in different directions can be intensively analysed, therefore providing precise information about the local rate of strain and rate of shear at a spatial point at a certain time point.

Special advantages provides an embodiment of the present invention, in which the step of Applying the processing algorithm comprises the calculation of the Jacobian matrix with respect to each one of the three spatial dimensions. Such an embodiment of the present invention provides the advantage that the movement of the voxel in each of the three spatial dimensions are considered, therefore providing a precise information about the deformation of the material in the voxel. Thus, the thickening and deformation of the wall of the heart and/or a region of the wall of the heart can be precisely tracked.

According to a further embodiment of the present invention the step of Applying the processing algorithm comprises performing an Eigensystem decomposition of the input parameters or performing an Eigensystem decomposition of a variable derived from the input parameters. The Eigensystem decomposition comprises determining the Eigenvalues and/or Eigenvectors. Such an embodiment of the present invention provides the advantage of providing the principal directions of local strain-rate and their magnitude.

According to a further embodiment of the present invention the step of Calculating the at least one disease parameter comprises the step of dividing an absolute value or magnitude of the rotation parameter by at least one Eigenvalue, wherein the at least one Eigenvalue results from the Eigensystem decomposition of a variable derived from the set of input parameters. Especially the absolute value or magnitude of the rotation parameter can be compared with a product of the number two with a positive Eigenvalue (of the strain-rate-tensor) or with a product of the negative number "−2" with the negative Eigenvalue (of the strain-rate-tensor), especially wherein the third Eigenvalue is zero. If this product on the basis of the Eigenvalues is equal to or close to the magnitude or absolute value of the rotation parameter, it can be concluded that a simple shear deformation is present. Such an embodiment of the present invention provides the advantage that the pure shear deformation of the considered volume element can be easily determined.

Furthermore, according to a special embodiment of the present invention the step of Calculating comprises calculating the disease parameter on the basis of the rotation parameter and at least the Eigenvalue, especially the most positive of the SRT. More specifically, the disease parameter can be calculated by multiplying the value of 0.5 with the absolute value of the rotation parameter, divided by the positive eigenvalue of the strain-rate-tensor. The smaller a deviation of the disease parameter from the value of 1 is, the larger is the proportion of the simple shear at the measured deformation. I.e., where the disease parameter is equal to the value of 1 and no relevant additional rotation is present a pure simple shear is present. Where the disease parameter is equal to zero there is no relevant simple shear deformation present. Such an embodiment of the present invention provides very precise information about the type of the cardiac disease due to the combination of the information from the rotation parameter as well as the information from the strain-rate-tensor.

According to a further embodiment of the present invention, in the step of Reading in a set of input parameters is read in, which was recorded by means of a magnetic resonance imaging apparatus. Such an embodiment of the present invention provides the advantage that the disease parameter can be calculated on a very precise set of input parameters which additionally can be obtained by a technically adult method for measuring vital parameters.

In order to obtain a precise disease parameter for more or all regions of the heart or in view of deeply analysing the motion of the heart in a timeline, a special embodiment of the present invention can be used, in which the steps of Reading in, Applying and Calculating are preformed consecutively for sets of input parameters representing the velocity of motion of voxels of different regions of the heart at a predefined time point and/or representing the velocity of motion of a voxel of a region of the heart at different predefined time points. Such an embodiment of the present invention provides the advantage of covering greater regions of the heart or longer time intervals in order to closely analyse the type of cardiac disease of a patient.

According to another embodiment of the present invention the method comprises a step of Analysing the disease parameter by comparing the disease parameter with a reference value and/or reference value interval in order to output a proposal for a specific cardiac disease. Such an embodiment of the present invention provides the advantage that by comparison of the disease parameter with a (predefined) reference value (for example taken from a precalculated or previously measured list of reference values) hint on a special type of cardiac disease can be given to the physician who analyses the patient. By such a preprocessing of the disease parameter prior to a display of this disease parameter to the physician the physician can be exculpated from analysing the data presented to him/her.

The apparatus can presently be considered as an electrical device or computerized system which is configured to process sensor signals and, dependently thereof, provide control and/or data signals. The sensor signals can for example be signals of a sensor of a medical device respectively, or of the sensor which is embedded in a medical device. The sensor signals can be considered the sensor signals of a magnetic resonance sensor or an echo sensor or the like. The control and/or sensor signals can be considered to be signals which are provided to a control or processing unit or processor which is configured to perform the above-mentioned method in separate instances or subunits. Such subunits can be for example be configured as signal processors, computer processors or microcontrollers which are capable of performing mathematical algorithms.

Furthermore, an embodiment of the present invention implemented as a computer program project or computer program with program code provides advantages, wherein the computer program product or the computer program with program code is stored on a machine readable carrier for a storage medium as for example a semiconductor storage, a disk storage or an optical storage. The computer program product or the program with program code can be configured for performing and/or controlling the steps of the method according to a previously described embodiment of the present invention, especially if the program product or program is run on a computer or a respectively configured apparatus.

BRIEF DESCRIPTION OF THE DRAWINGS

Embodiments of the approach presented here are described and depicted in detail with respect to the following figures and description. Shown is in FIG. 1 a schematic view of a medical device comprising an apparatus according to an embodiment of the approach presented here.

DETAILED DESCRIPTION

Figure 1:
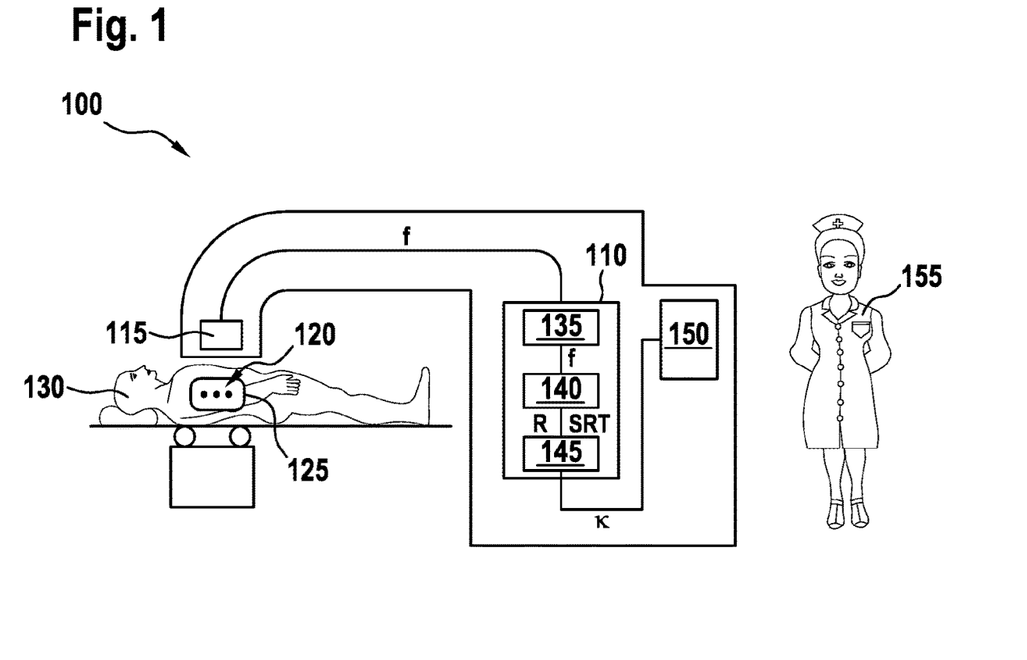

FIG. 1 shows a schematic view of a medical device 100 comprising an apparatus 110 according to an embodiment of the approach presented here. The medical device 100 comprises a sensor 115 which is configured for measuring a set of input parameters f, which for example represents the movement of voxels 120 of a region of a heart 125 or of the heart 125 itself. It has to be noted, that the proportions of the heart 125 of a patient 130 is shown only schematically in FIG. 1 for illustration reasons. To be more specific, the sensor 115 provides a field of velocity vectors as set of input parameters f, in which each velocity vector represents the velocity of the respective voxel 120 in spatial dimensions at the time point of measurement. However, the sensor 115 is configured to provide the set of input parameters f such that the velocity vectors for each of the voxels 120 during the measurement are provided for the same time point respectively the same time interval, which is necessary for measuring the velocity for each voxel. Thus, the time point can also be considered as a (small) time interval for capturing the values for the velocities of the voxels for a set of input parameters. The set of input parameters f is then transferred to the apparatus 110 according to an embodiment of the present invention. The apparatus comprises an interface 135 for reading in the set of input parameters f. Furthermore, the apparatus 110 comprises a unit 140 for applying a processing algorithm on the set of parameters f in order to obtain at least a rotation parameter R and/or at least a strain-right-tensor SRT. The rotation parameter R represents the local curl of the set of input parameters f, wherein the strain-rate-tensor SRT represents the local rate of strain at a certain special point, especially at a voxel, at a certain time point. The apparatus 110 furthermore comprises a unit 145 for calculating that disease parameter κ on the basis of the rotation parameter R and/or the strain-rate-tensor SRT. The disease parameter κ can then be provided to a display unit 150, which can display one or more disease parameters (for example for different regions of the heart 125 and/or for several, for example consecutive, time points) to a physician 155 in order to provide information from which the type of cardiac disease can be concluded by the physician 155.

In consideration of the above-described embodiment of the present invention, the so called Keirometry can be seen as depending on a 3D velocity map or voxel velocity vectors as set of input parameters, which can be for example obtained by a custom-made MRI (MRI=Magnetic resonance imaging) sequence which was developed in close interdisciplinary collaboration by the inventors. In principle, the so called keirometry can also be performed on 3D myocardial velocity maps obtained by other techniques for data acquisition as for example echocardiography, other MRI-techniques or other measurement techniques that provide a 3D myocardial velocity map. The herein described embodiment of the invention as the so called keirometry uses a special inventive analysis method for 3D myocardial velocity fields.

Figure 2:
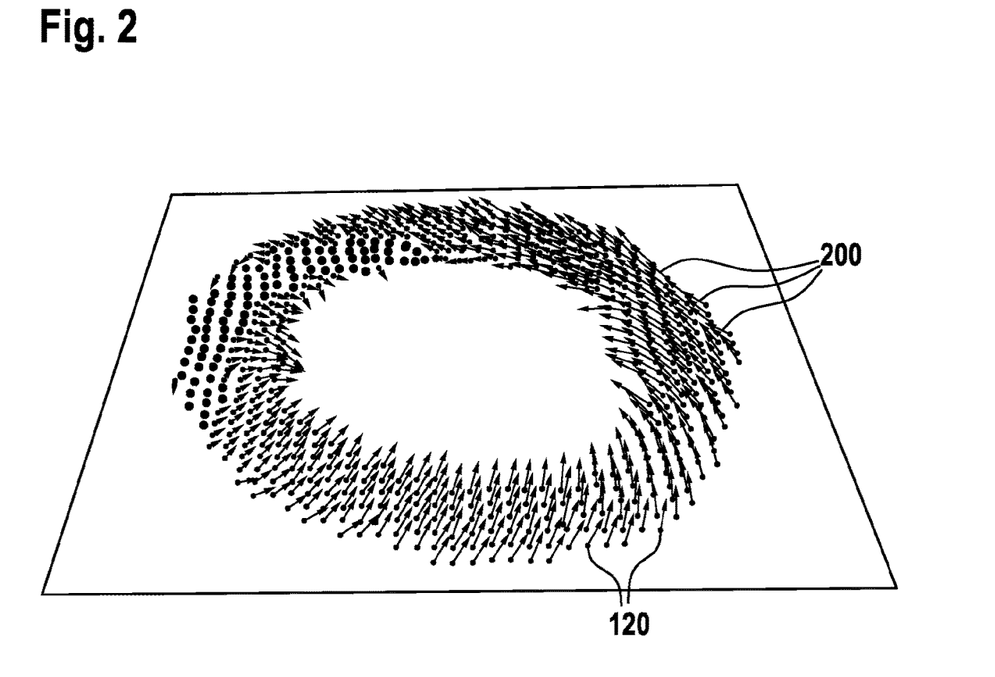
FIG. 2 a diagram of an example of a set of input parameters as velocity vectors.

FIG. 2 shows a diagram of an example of a set of input parameters as velocity vectors 200. This velocity vectors represent a short axis slice of the left ventricle of a person 130 in mid-systole. Arrows represent the velocity vectors 200, which depict the voxel wise three-dimensional velocity of the myocardium with different magnitude. The data shown in FIG. 2 was acquired by means of said custom-made MRI sequence.

As mentioned above the assessment of myocardial kinematics and especially myocardial shearing motion requires for example a three-dimensional motion analysis with sufficiently high temporal and spatial resolution with very good data quality.

For the experimental assessment of cardiac mechanics a cardiac 4D Flow MRI sequence was developed, which is able to measure 3D myocardial velocity fields with voxel wise 3D velocity information for the analysis of myocardial motion, (as shown in FIG. 2) over the whole cardiac cycle using velocity phase encoding. Thus several sets of input parameters as the field of velocity vectors are generated each for example for different time points and/or different regions of the heart wall.

The origin of the so called keirometry (Greek: keirein: to shear, to metron: the measure) according to a special embodiment of the present invention is determining a tensor given by the Jacobian matrix Df of the considered velocity field f at any point of the investigated field of view:

$$Df = \begin{pmatrix} \frac{\partial f_1}{\partial x_1} & \cdots & \frac{\partial f_1}{\partial x_n} \\ \vdots & \ddots & \vdots \\ \frac{\partial f_m}{\partial x_1} & \cdots & \frac{\partial f_m}{\partial x_n} \end{pmatrix},$$

wherein f represents a velocity vector field as example of a set of input parameters with components $f_1$-$f_m$ and coordinates $x_1$-$x_n$, in the present case: m=n=3, and wherein δ denotes a partial derivative.

This Jacobian matrix Df can be decomposed in parts describing different kinematic features of the local motion. Important decompositions for keirometry are the symmetric component, the strain-rate-tensor SRT describing the local rate of strain (=deformation) at a certain spatial point at a certain time point, $$SRT = \frac{1}{2}(Df + Df^T)$$

wherein $Df^T$ denotes a transposed Jacobian matrix and the antisymmetric component, the rotational-rate-tensor RRT describing the local rate of rotation at a certain spatial point at a certain time point, $$RRT = \frac{1}{2}(Df - Df^T)$$

These tensors contain the whole information on the local three dimensional rotational-rate and the local three dimensional strain-rate. The different components of local shear-rate are defined as the different local spatial derivatives of the velocity components and are as such contained within the SRT.

From the correlation of these two tensors (SRT and RRT) information can be derived on the local shearing mechanics of the investigated field. First the orthogonal eigensystem of the SRT is calculated in this embodiment by solving the classical eigenvector problem:

$$SRT f = \lambda f$$

wherein $\lambda$ denotes the eigenvalue.

This eigensystem allows analysing the principal directions of local strain and their magnitude.

Then we calculate the local curl of the field:

$$R = \text{curl} = \nabla \times f$$

wherein $\nabla$ represents the Nabla-operator and × denotes the cross product.

For the following considerations the distinction between so called pure shear and so called simple shear is of interest.

Figure 3A:
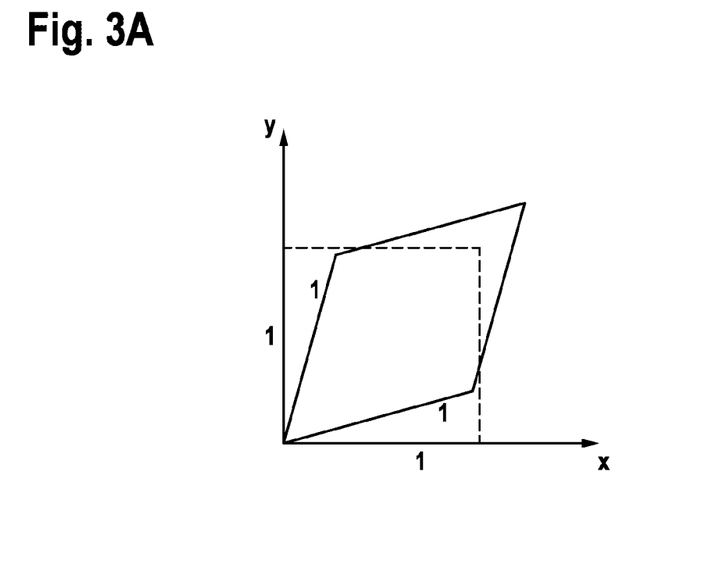
FIG. 3A a diagram, depicting that pure shear is a shearing deformation without any rotational component.

FIG. 3A shows a diagram, depicting that pure shear is a shearing deformation without any rotational component.

Figure 3B:
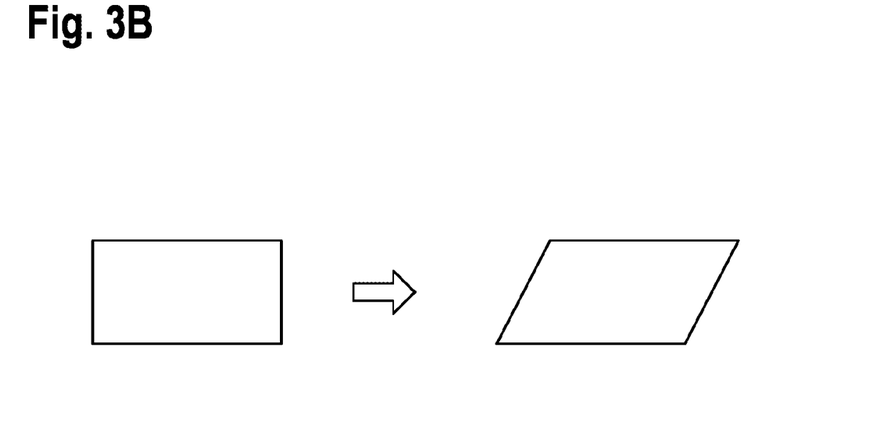
FIG. 3B a diagram, depicting that simple shear is a shearing deformation.

FIG. 3B shows a diagram, depicting that simple shear is a shearing deformation, which occurs for example in the case of shearing between two layers. FIG. 3B thus illustrates the so called simple shear as shearing between two layers. It is a simplified depiction of simple shear by for example cutting planes through a deformed cuboid.

Figure 3C:
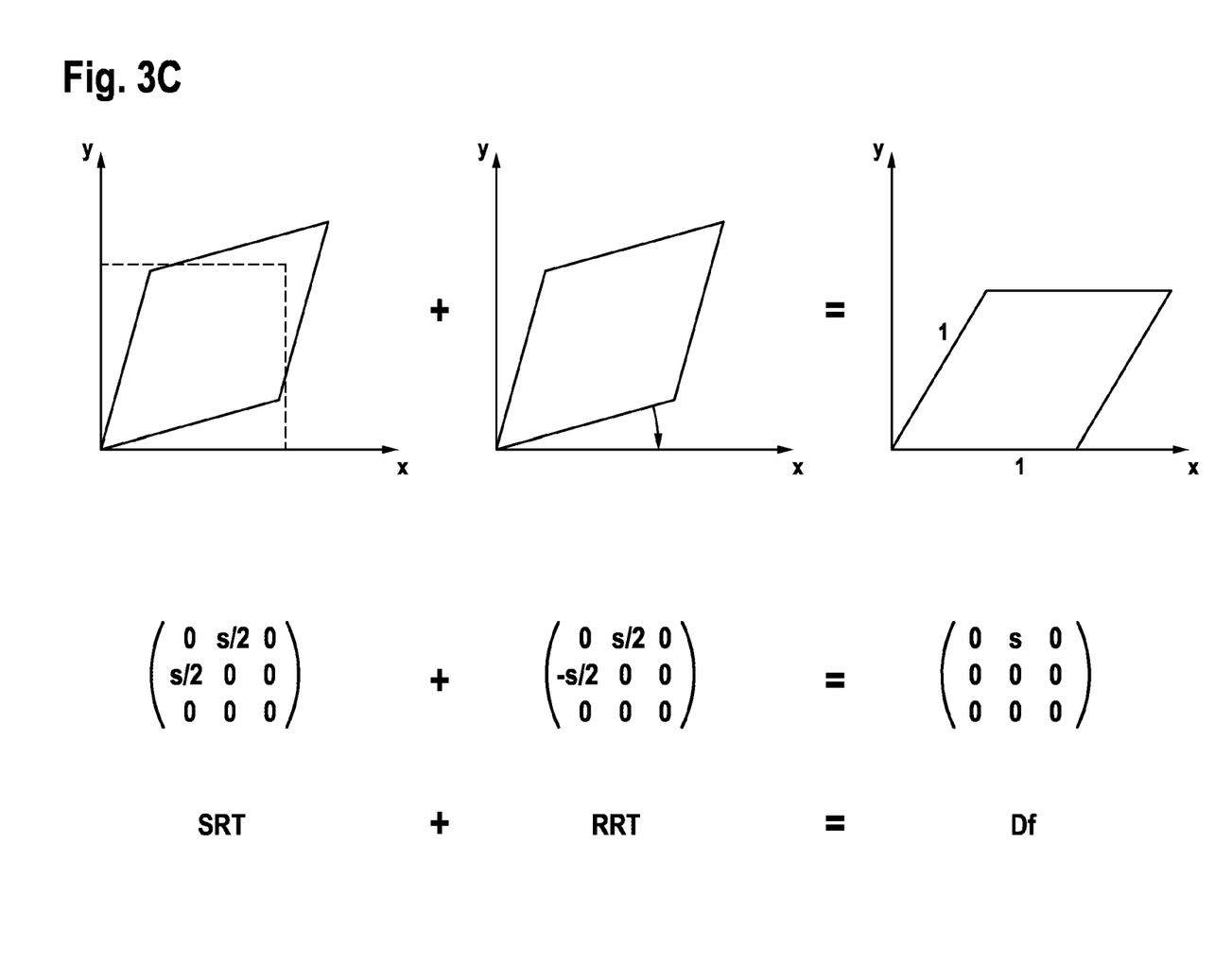
FIG. 3C an illustration for explanation of a decomposition of the so called Simple shear.

FIG. 3C depicts an illustration for explanation of a decomposition of the so called Simple shear, which contains also a rotational component (rigid body rotation) besides the pure shear component. Simple shear can be decomposed in these two components by decomposing Df into the SRT, which represents the pure shear, and the RRT which represents the rotational component. In the lower part of the illustration of FIG. 3C a decomposition algorithm is shown in order to further explain the decomposition of the simple shear into the pure shear component SRT and the rotational component RRT in mathematical terms. FIG. 3C therefore can be considered as an illustration of the decomposition of simple shear: simple shear deformation, which is occurring in the sliding of two layers (and which we expect to occur between intramyocardial layers) can be decomposed into its pure shear component contained within the SRT and its rotational component contained within the RRT.

If now a closer look is taken at the SRT and the RRT of a so called simple shearing deformation (e.g. horizontal sliding of layers, confer FIGS. 3B and 3C), it can be found that it is composed of a so called pure shearing deformation (contained within the SRT) and a rotational component (contained in the RRT respectively Curl).

Just a simple example clarifies this:

The local Jacobian Df of a velocity field depicting such a simple shear deformation of a cuboid as illustrated (in FIG. 3B or 3C) by cuts through a deformed cuboid is given by: Df=(0 s 0; 0 0 0; 0 0 0), where s is the shear rate.

Then the local SRT=(0 s/2 0; s/2 0 0; 0 0 0) and the local RRT=(0 s/2 0; −s/2 0 0; 0 0 0) (as in FIG. 3C).

Analysing these tensors SRT and RRT in a simple shear deformation a pure shear deformation can be found contained within the SRT, with two eigenvectors respectively oriented in 45 degrees from the axes of the shearing plane (i.e. the shearing direction and the axis perpendicular to the shearing layers) and with the correlation $$|\text{Curl}| = 2\lambda_1 = -2\lambda_2 \qquad (1)$$

where $\lambda_1$ is the positive eigenvalue of the SRT and $\lambda_2$ is the negative eigenvalue of the SRT. $\lambda_3$ is 0 in this case.

Figure 4:
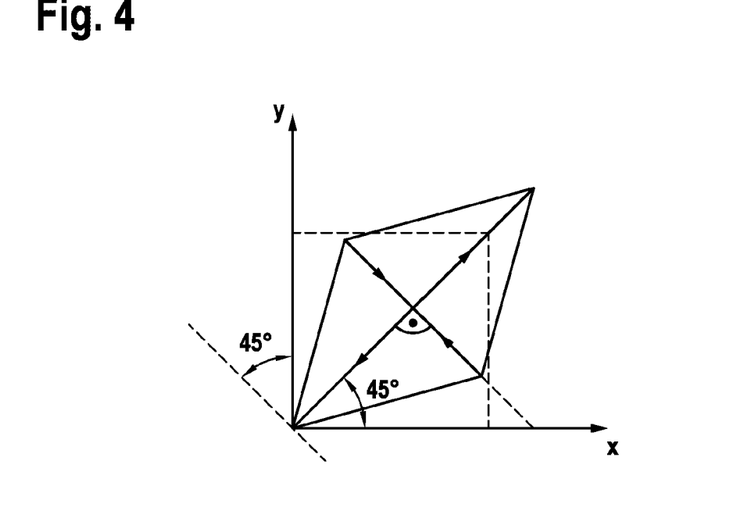
FIG. 4 an illustration of the principal strain axes of an SRT.

As illustrated in FIG. 4, in the example presented here, eigenvectors oriented in 45 degrees from the x- and y-axis can be found. The eigenvectors in the present example have eigenvalues $\lambda_1 = s/2$ and $\lambda_2 = -s/2$ and in this case Curl=s.

FIG. 4 depicts an illustration of the principal strain axes of an SRT: the axes of principal strain are represented by the eigenvectors of the SRT and are oriented in 45 degrees from the axes of the original cube, more precisely: 45 degrees from the shearing direction (in this case the x-direction) and 45 degrees from the direction perpendicular to the shearing layers.

According to a preferred embodiment of the present invention a disease parameter κ can be calculated in a respective step of calculating. The rate of the local pure shear is dependent on the chosen coordinate system. Thus the eigensystem of the local SRT as coordinate system can be chosen. And in this eigensystem there is no more shear-rate. But if a simple shear is present, e.g. shearing between layers, then there is for example an additional rotational component. And this component is invariant under transformation of coordinates. It is contained within the RRT or can simply be calculated as the local Curl and shows the mentioned correlation with factor 2 and factor −2 with the eigenvalues of the SRT (according to equation 1). If there is an additional rigid rotation within the considered field of view thus with a rotational curl due to this rigid rotation directly additive to the Curl due to simple shearing, a correction can be applied.

When acquiring myocardial velocity fields in vivo at the beating heart the actual local direction of possible intramyocardial shearing motion is not known. Since shear-rate is dependent on the coordinate system it is difficult to identify and to quantify shearing motion. The so called Keirometry as an embodiment of the here presented approach, considering not only the SRT but also the RRT, is able to identify and to quantify simple shearing motion without a previously known local shearing direction.

Performing the so called keirometry means to preferably investigate both in combination: the pattern of the eigensystem of the local SRT and the local Curl. In a real experiment, there will mostly be a combination of pure deformation (e.g. compression in one direction and dilation in other directions) and simple shear deformation (e.g. shearing between layers).

To quantify the proportion of these two components the disease parameter κ is introduced. For example, the disease parameter can be calculated by:

$$\kappa = \frac{1}{2}|\text{Curl}|/\lambda_1$$

wherein | . . . | denotes a magnitude or an absolute value.

The parameter κ reflects the proportion of the two kinds of deformation and the appropriateness of the relation in equation (1) within the measured field of view.

If there is only shearing between layers i.e. simple shear and no pure deformation, then equation (1) is fully appropriate and
κ=1 (as in the previous example depicted in FIGS. 3B and 3C)

If there is only pure deformation without any simple shear (e.g. without any shearing between layers), then
κ=0

Thus the disease parameter κ especially reflects the proportion in relation to overall deformation of local layer shearing and local pure deformation within the considered field of view.

In the case of vastly dominating layer shearing, the pattern of the SRT-eigensystem and the Curl is given by equation (1). This means that the parameter κ should be close to 1 (or at least markedly increase with a tendency towards 1 in the case of starting layer shear).

The previously described approach, the so called Keirometry, means preferably an integrative assessment of both, the local eigensystem of the SRT and the local Curl (contained within the eigensystem of the RRT, by the way). Keirometry is for example identifying, analysing and quantifying the local shearing motion within the field of view by investigating these features.

In summary, the local Curl in correlation with the pattern of the local SRT-eigensystem can be used as a measure for the local simple shear rate. This shearing causes a strain of the considered volume element. This strain effect caused by simple shearing is not only quantitatively related to the rotational curl (see equation (1)) but shows also a certain pattern of the SRT eigensystem (i.e. quantitatively dominating $\lambda_1$ and $\lambda_2$ with $|Curl|=2\lambda_1=-2\lambda_2$). Experimentally depicting this shearing-specific pattern of the eigensystem and the relation of equation 1 with quantitatively dominating $\lambda_1$ and $\lambda_2$ a very strong experimental evidence for the hypothesis can be achieved, that shearing motion is the main mechanism of strain (thickening and thinning) within the myocardium. The approach presented here in a preferred embodiment, i.e. Keirometry, will not only be the key to tackle this hypothesis but with the Curl it will also provide a direct and absolute measure for the quantification of local myocardial shear-strain over the whole cardiac cycle with several control parameters.

Thus investigations by means of keirometry can be made, if intra-myocardial simple shearing (e.g. shearing between layers) is the main generator of local strain (thickening and thinning) at any time point of the cardiac cycle, and quantify the effect by means of Curl and κ and investigate if this dominating role of shearing is changing over the cardiac cycle in health and disease.

The previously described approach can be used for direct translation to volunteer and patient studies. This method requires zero invasivity, not even the application of contrast agent. It is applicable to any measured 3D velocity field, acquired for example by MRI-techniques or also echo-techniques or other techniques that provide a 3D myocardial velocity field with sufficient data quality. It is applicable to the whole cardiac cycle. Therefore, keirometry constitutes a strong analysis modality for myocardial motion analysis, which is equally applicable to systole and diastole and has the potential for being used not only with MRI data acquisition techniques but also with data acquired by echocardiographic (e.g. 3D speckle tracking echo) or any other data acquisition techniques.

Figure 5:
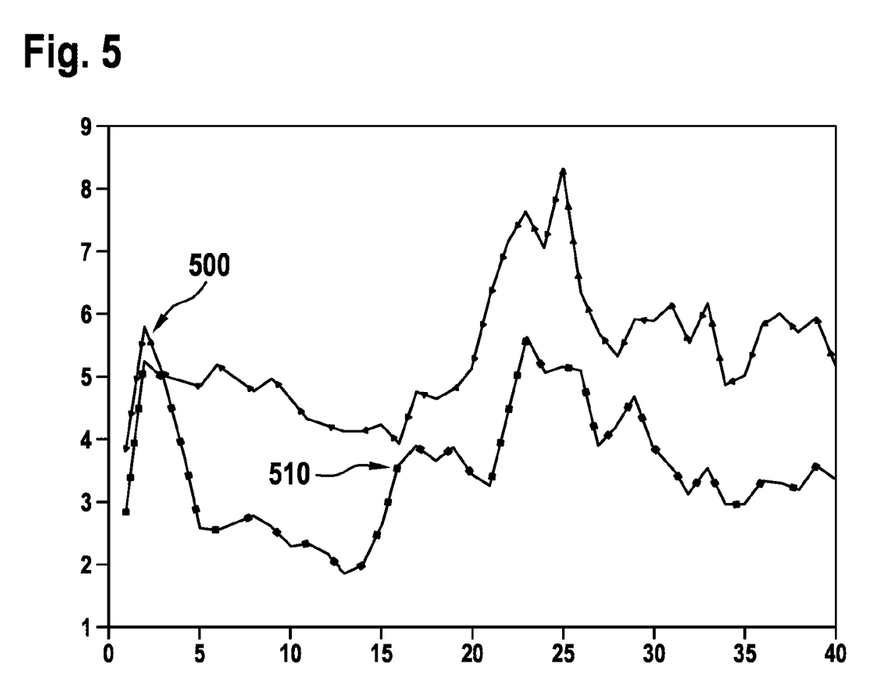
FIG. 5 a diagram of an exemplary healthy volunteer data.
Figure 6:
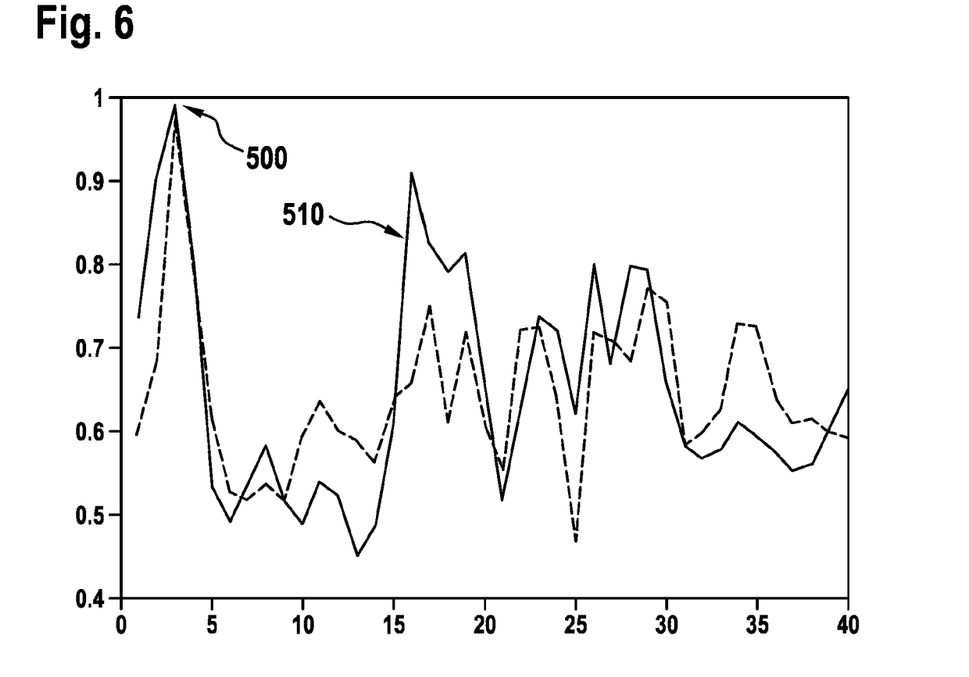
FIG. 6 a diagram of an exemplary healthy volunteer data.

In the volunteers measured up to now a marked predominance of shearing deformation particularly in early systole (starting from time point 1) and in early diastole (starting from time point ~15) in a biphasic pattern is found, clearly visible in FIGS. 5 and 6.

FIG. 5 shows a diagram of exemplary healthy volunteer data. On the x-axis time is depicted (1 unit=20 ms) and on the y-axis strain-rate respectively rotational-rate in 1/sec is depicted. Furthermore, the beginning of the systole 500 and the beginning of the diastole 510 is also depicted in FIG. 5. The line in triangles depicts the mean of the voxel wise maximum positive eigenvalues of endocardilal voxels, i.e. the voxel wise magnitude of maximum extension and the line in rectangles depicts the mean of the half magnitude of the rotational Curl. The action depicted in time points 1-14 corresponds to systole. The action depicted in time points 15-40 corresponds to diastole. Clearly visible is that during early systole and early diastole the rotational curl (line in rectangles) and thus the disease parameter κ is increasing, indicating vastly predominating shearing deformation in these parts of the cardiac cycle. Furthermore, a biphasic pattern of strain rate and corresponding shearing predominance in diastole can be seen. It seems very promising to investigate alterations of this diastolic shearing pattern in the still not well-classified diastolic dysfunction, where there is still no specific therapy after many inconclusive clinical trials based on echocardiographic parameters.

FIG. 6 shows a diagram of exemplary healthy volunteer data. On the x-axis time is depicted (1 unit=20 ms) and on the y-axis the disease parameter κ is depicted. Furthermore, the continuous line represents the disease parameter κ of endocardial voxels and the dashed line represents the disease parameter κ of epicardial voxels. The action depicted in time points 1-14 corresponds to systole. The action depicted in time points 15-40 corresponds to diastole. Clearly visible is that during early systole and early diastole κ is markedly increasing (more accentuated in the endocardial region: continuous line), indicating vastly predominating shearing deformation in these parts of the cardiac cycle. Furthermore, a biphasic pattern of strain rate and corresponding shearing predominance in diastole can be seen. It seems very promising to investigate alterations of this diastolic shearing pattern in the still not well-classified diastolic dysfunction, where there is still no specific therapy after many inconclusive clinical trials based on echocardiographic parameters.

In can be concluded that the new method, called keirometry, is well applicable to myocardial analysis and provides already strong experimental evidence for the predominant role of intramyocardial shearing motion, particularly in early systole, and biphasically in early and mid-diastole, as shown in the FIGS. 5 and 6. It seems very promising to investigate alterations of this diastolic shearing pattern (FIGS. 5 and 6) in the still not well-classified diastolic dysfunction, where there is still no specific therapy after many inconclusive clinical trials based on conventional echocardiographic parameters, suggesting that these conventional echo-parameters do not provide a relevant stratification of diastolic dysfunction.

Taking a look at the 3D field of the voxel wise eigenvectors corresponding to the maximum negative eigenvalue in diastole i.e. local direction and magnitude of maximum instantaneous thinning at the exemplary time point 22 in mid-diastole (FIG. 7), it is possible to validate visually the excellent quality of the data and realistic depiction of diastolic myocardial deformation.

Figure 7:
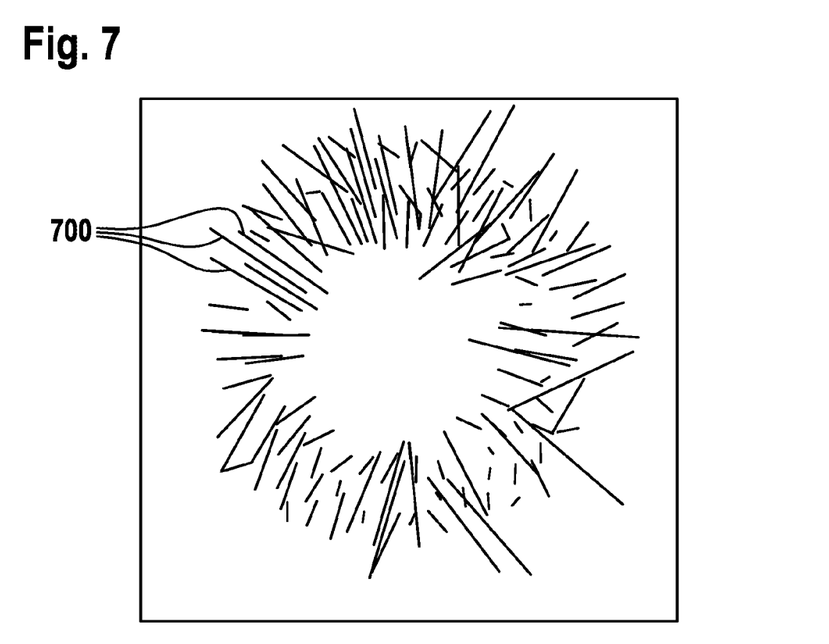
FIG. 7 a diagram of an exemplary healthy volunteer data.

FIG. 7 shows a diagram of exemplary healthy volunteer data, wherein the left ventricular 3D short axis slab in mid diastole at time point 22 is depicted. The 3D field of the voxel wise eigenvectors 700 are shown, corresponding to the maximum negative eigenvalue in diastole i.e. local direction and magnitude of maximum instantaneous thinning at the time point 22 in diastole. The length of the lines 700 reflect the magnitude i.e. in this case the maximum negative eigenvalues. It has to be noted, that as eigenvectors have no unique polarity, eigenvectors are represented as lines instead of arrows. Clearly visible in this figure is the excellent data quality and realistic depiction of diastolic myocardial deformation.

Figure 8:
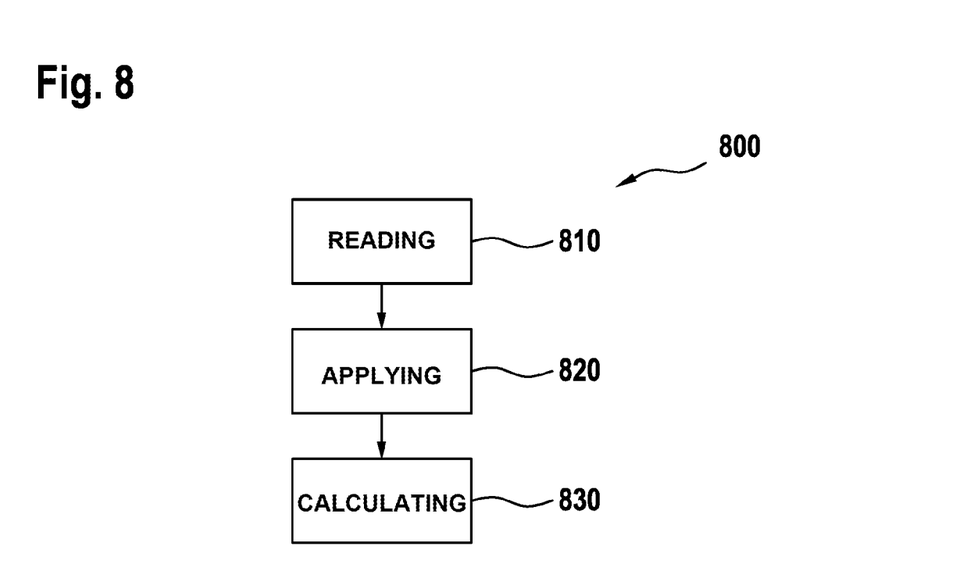
FIG. 8 a flow diagram of a method for determining a disease parameter describing a type of cardiac disease according to an embodiment of the present invention Same or equal elements are denoted by same or equal reference numerals, wherein a repeated description is omitted due to clarity reasons.

FIG. 8 shows a flow diagram of a method 800 for Determining a disease parameter describing a type of cardiac disease according to an embodiment of the present invention. The method 800 comprises step of Reading in 810 a set of input parameters, wherein the input parameters represent a field of velocity vectors, each velocity vector representing a velocity of motion of a voxel of a region of the heart at a predefined time point. Furthermore, the method 800 comprises step of Applying 820 a processing algorithm on the set of input parameters in order to obtain at least a rotation parameter and/or at least a strain-rate-tensor, the rotation parameter representing the curl of the set of input parameters and the strain-rate-tensor representing a local rate of strain at a certain special point at a certain time point. Finally the method 800 comprises step of Calculating 830 the disease parameter on the basis of the rotation parameter and/or the strain-rate-tensor.

As the here described approach, called keirometry is a novel method for the investigation of myocardial motion in systole and diastole, it opens up a new field of myocardial imaging. The approach, Keirometry, is able to reveal a hitherto unknown physiological effect of myocardial motion, which can be quantified directly and non-invasively, and thereby provides a strong and fundamentally new tool to investigate myocardial motion in various pathologies including the still poorly understood but clinically highly relevant diastolic heart failure. Furthermore, the method is not restricted to MRI data acquisition, but can in principle also be applied to appropriate echocardiographic datasets or datasets from other acquisition techniques.

The invention claimed is:

1. A system configured for determining a disease parameter describing a type of cardiac disease, comprising:
 a sensor configured to measure a set of input parameters, wherein the input parameters represent a field of velocity vectors measuring 3D myocardial velocity fields with voxel wise 3D velocity information, each velocity vector representing a velocity of motion of a voxel of a region of a heart at a predefined time point or time interval, and wherein a velocity vector depicts a voxel wise three-dimensional velocity of the myocardium with different magnitude; and
 a computer comprising:
 an interface configured for reading in the set of input parameters,
 a first computer processor configured for applying a processing algorithm on the set of input parameters in order to obtain at least a rotation parameter and at least a strain-rate-tensor, the rotation parameter representing local curl of the set of input parameters and the strain-rate-tensor representing local rate of strain at a certain spatial point at a certain time point or time interval,
 wherein the strain-rate tensor (SRT) is calculated by a Jacobian matrix (Df) of the considered field of velocity vectors (f), using the formula SRT=½(Df+Df$^T$) wherein Df$^T$ denotes a transpose of the Jacobian matrix and wherein the rotation parameter is derived from the formula curl=∇× f wherein ∇ represents the Nabla-operator and × denotes the cross product or wherein the rotation parameter is calculated using the rotational rate tensor (RRT) formula RRT=1(Df-Df$^T$);
 a second computer processor configured for calculating at least the disease parameter on the basis of the rotation parameter and the strain-rate-tensor,
 wherein the second computer processor is configured for calculating the disease parameter by dividing an absolute value of the rotation parameter by at least one eigenvalue, the at least one eigenvalue resulting from solving the eigenvector problem SRT f=λf, wherein λ, denotes the at least one eigenvalue and wherein the disease parameter reflects a proportion to overall deformation of local layer shearing with regard to local pure deformation,
 wherein the second computer processor is further configured for comparing the disease parameter to a predefined reference value; and
 a display connected to the second computer processor, wherein the display is configured to output the disease parameter and a proposal for a type of cardiac disease determined based on the comparison.

2. A system apparatus according to claim 1, wherein the first computer processor is configured for calculation of at least the Jacobian matrix from the set of input parameters, in order to calculate the strain-rate-tensor.

3. A system according to claim 1, wherein the first computer processor is configured for calculation of the Jacobian matrix with respect to each of three spatial dimensions (xI, x2, x3).

4. A system according to claim 1, wherein in the interface, the set of input parameters were recorded by a magnetic resonance imaging (MRI) apparatus.

5. A system according to claim 1, wherein the interface and the first and second computer processor are configured for consecutively processing sets of input parameters representing the velocity of motion of voxels of different regions of the heart at a predefined time point or time interval, and/or representing the velocity of motion of voxels of the region of the heart at different predefined time points or time intervals.

* * * * *